United States Patent [19]
Fagan et al.

[11] Patent Number: 5,545,132
[45] Date of Patent: Aug. 13, 1996

[54] HELICALLY GROOVED BALLOON FOR DILATATION CATHETER AND METHOD OF USING

[75] Inventors: John R. Fagan, Pepperill; Jeffrey Kling, Tewksbury, both of Mass.

[73] Assignee: C. R. Bard, Inc., Murray Hill, N.J.

[21] Appl. No.: 171,061

[22] Filed: Dec. 21, 1993

[51] Int. Cl.⁶ .................................................. A61M 29/00
[52] U.S. Cl. ............................................. 604/96; 606/194
[58] Field of Search ............................. 604/96, 101, 52, 604/53, 280–282, 264; 606/191, 194, 195

[56] References Cited

U.S. PATENT DOCUMENTS

| 4,950,232 | 8/1990 | Ruzicka et al. | 604/43 |
| 5,250,070 | 10/1993 | Parodi. | |
| 5,295,959 | 3/1994 | Gurbel et al. | 604/96 |
| 5,295,995 | 3/1994 | Kleiman | 606/194 |
| 5,306,246 | 4/1994 | Sahatjian et al. | 604/96 |
| 5,308,356 | 5/1994 | Blackshear, Jr. et al. | 606/194 |
| 5,348,538 | 9/1994 | Wang et al. | |
| 5,403,340 | 4/1995 | Wang et al. | |

FOREIGN PATENT DOCUMENTS

| WO9317748 | 8/1993 | WIPO. |
| WO9317748 | 9/1993 | WIPO. |

Primary Examiner—John D. Yasko
Attorney, Agent, or Firm—Bookstein & Kudirka, P.C.

[57] ABSTRACT

A dilatation balloon having at least one helical groove disposed in at least a portion of the dilating surface of the dilatation balloon is mounted on the distal end of a catheter shaft. Multiple helical grooves may be provided in the dilatation balloon extending parallel to each other or opposite to each other in the dilating surface. Each helical groove has a pitch, width and depth. According to one aspect of the invention, the pitch, width and depth of the helical groove, as well as the number of grooves, are selected to allow perfusion of blood past the dilatation catheter when the dilatation balloon is inflated in a blood vessel. According to another aspect of the invention, the pitch, width, and depth of the helical groove, as well as the number of grooves, are selected so that the dilatation balloon conforms to a tortuous blood vessel and does not straighten the blood vessel during dilation. According to another aspect of the invention, the pitch, width, and depth of the helical groove, as well as the number of grooves, are selected to control the diametrical compliance of the dilatation balloon. The pitch, width, and depth of the helical groove may be selected to provide both conformance to the shape of tortuous blood vessels and diametrical compliance. The helical groove also permits the dilatation balloon to deflate without "winging", i.e., forming undesirable flat folds that extend outward from the rest of the catheter.

70 Claims, 4 Drawing Sheets

HELICALLY GROOVED BALLOON FOR DILATATION CATHETER AND METHOD OF USING

FIELD OF THE INVENTION

The present invention relates generally to a dilatation catheter having a dilatation balloon mounted on the distal end of the catheter. The balloon enables perfusion past the balloon, flexibility through circuitous blood vessels, and control of balloon diameter as a function of inflation pressure.

BACKGROUND OF THE INVENTION

Most balloons used in dilatation catheters are designed to provide a uniform and controllable diameter over the length of the balloon. Typically, the dilatation balloon does not conform to the curved shape of a blood vessel during inflation of the balloon. The body of the balloon becomes straight and rigid as the balloon is inflated under pressure of an inflation liquid introduced through an inflation lumen communicating between the balloon and the proximal end of the catheter. Consequently, when inflated, the balloon tends to straighten the blood vessel at the site of the lesion. That is not desirable because the dilatation balloon may not effectively open the blood vessel or may cause additional damage to the blood vessel walls as a result of the straightening.

Additionally, when inflated, the dilatation balloon blocks blood flow through the blood vessel, thus limiting the length of time that the blood vessel may be dilated before chest pain requires the dilatation balloon to be deflated. Longer dilation times are desirable because conditions such as restenosis may tend to occur less frequently when longer dilation times are used.

Upon deflation, a dilatation balloon may contract in a manner that forms "wings." That is, rather than maintaining a circular cross-section upon deflation, the dilatation balloon deflates to form flat portions called wings that extend radially outward from the balloon. This so-called "winging" phenomenon is undesirable because it results in a larger crossing profile when locating the balloon in a stenosis.

Some dilatation balloons are designed to have diametrical compliance, that is, a change in diameter of the dilatation balloon as a function of inflation pressure. Dilatation balloon materials and designs are generally chosen to provide linear diametrical compliance, that is, a linear relationship between dilatation balloon diameter and inflation pressure. Typically, diametrical compliance is achieved by selecting a material for the balloon that stretches upon application of inflation pressure. However, conventional compliant dilatation balloons have no maximum size limitation and as a result increased inflation pressures cause the balloon to keep expanding, thereby risking injury to the blood vessel if overinflated.

It would be desirable, therefore, to provide dilatation balloons that avoid the foregoing difficulties.

SUMMARY OF THE INVENTION

The invention overcomes the disadvantages of the prior art by providing perfusion of blood past the dilatation catheter and avoidance of straightening of the blood vessel when the dilatation balloon is inflated. In addition, the diametrical compliance can be controlled and the dilatation balloon can be deflated without winging. The invention provides a dilatation catheter including a catheter shaft having a dilatation balloon mounted on the distal end of the shaft including at least one-helical groove disposed in at least a portion of the dilating surface of the dilatation balloon. Multiple helical grooves may be provided in the dilatation balloon extending parallel to each other or opposite to each other in the dilating surface.

Each helical groove has a pitch, width, and depth. In one aspect of the invention the pitch, width, depth, as well as the number of grooves, are selected to allow perfusion of blood past the balloon when the balloon is inflated in a blood vessel. In another aspect of the invention the pitch, width and depth of the groove, as well as the number of grooves, are selected so that the balloon is flexible longitudinally, even when inflated, so that it can conform to the curves in a blood vessel, to allow the blood vessel to retain most of its natural curvature during dilatation. In another aspect of the invention the pitch, width and depth of the helical groove, as well as the number of grooves, are chosen such that the diametrical compliance of the dilatation balloon can be controlled.

The helical groove also permits the dilatation balloon to deflate without "winging", i.e. forming undesirable flat folds that extend outward from the rest of the catheter.

The helical groove may extend over only a portion of the dilatation balloon to create zones of compliance (where the groove is located) and zones of non-compliance (where the groove is not located).

In addition, the pitch, width and depth of the helical groove may vary over the dilating surface of the dilatation balloon. If multiple helical grooves are provided, the pitch, width and depth of each groove may vary over the dilating surface of the dilatation balloon.

By using a material such as polyethylene terephthalate (PET), the diametrical compliance of the dilatation balloon is a linear function of inflation pressure up to a predetermined maximum balloon diameter. Even if inflation pressure is increased, the diameter of the dilatation balloon does not significantly increase above the maximum diameter.

The pitch, width and depth of the helical groove, as well as the number of grooves, may be selected to provide both conformance to the shape of circuitous blood vessels and diametrical compliance.

An object of the present invention is to provide an improved dilatation catheter balloon having a helical groove that allows the balloon to conform to the natural shape of tortuous blood vessels and avoids straightening the blood vessel during dilatation.

Another object of the present invention is to provide a dilatation catheter balloon that allows blood to perfuse past the balloon during dilation, to allow for longer dilation times.

Still another object of the present invention is to provide a dilatation catheter balloon that has linear diametrical compliance up to a predetermined maximum dilatation balloon diameter and no further diametrical compliance above the maximum diameter.

The features and advantages of the invention will be more readily understood from the following detailed description of the invention, which should be read in conjunction with the accompanying drawings.

BRIEF DESCRIPTION OF THE DRAWINGS

In the drawings, in which like elements have been given like reference characters,

3

Figure 1:
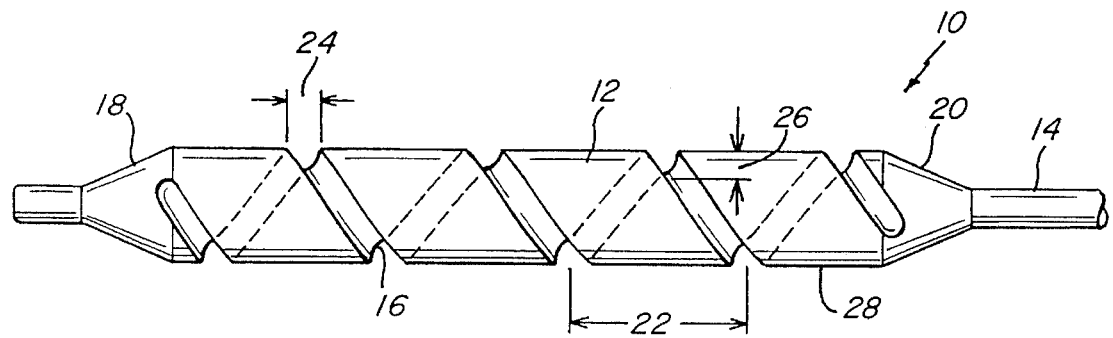
Figure 2:
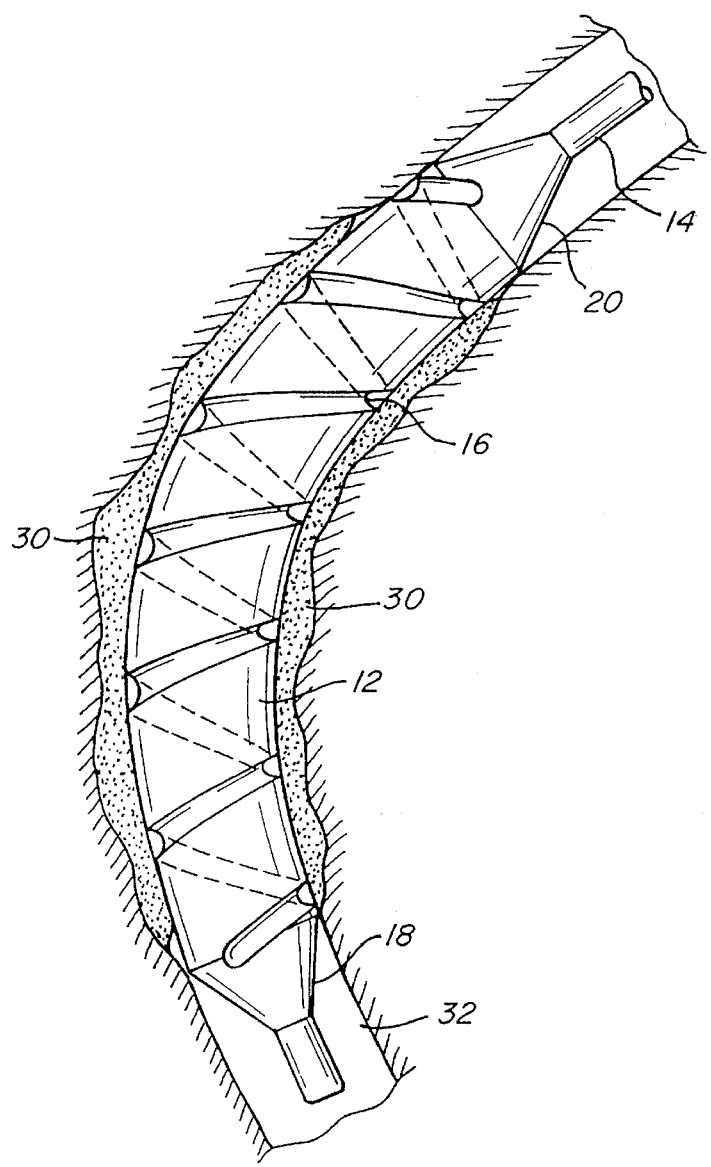
Figure 3:
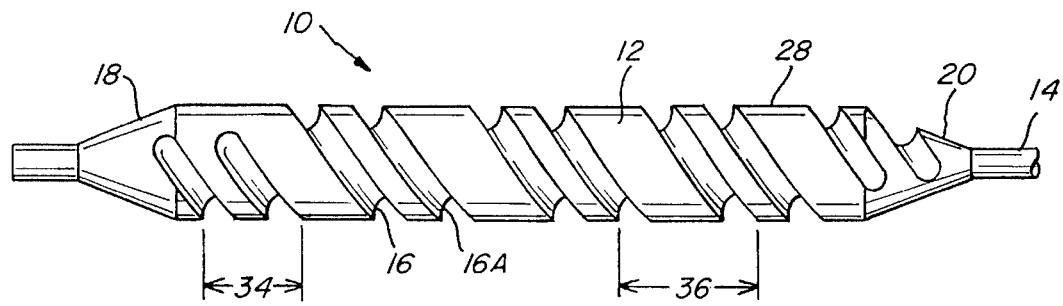
Figure 4:
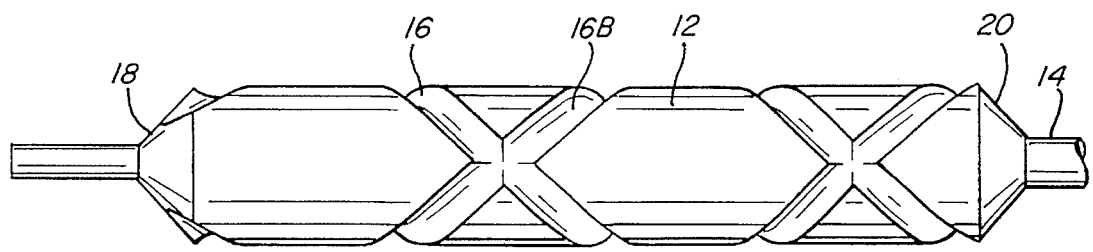
Figure 5A:
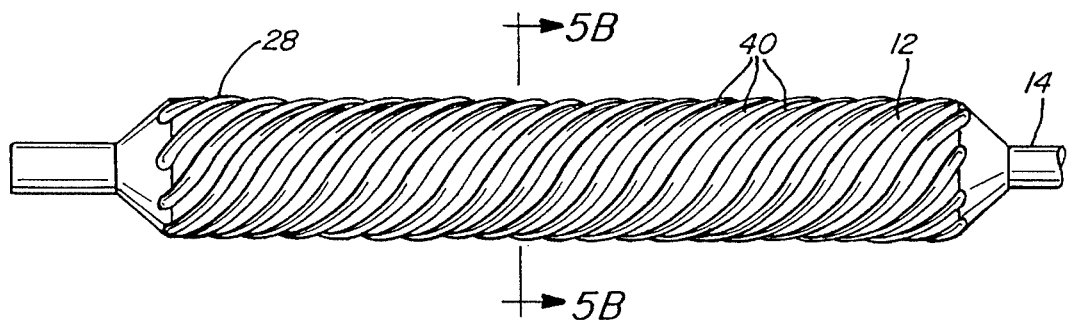
Figure 5B:
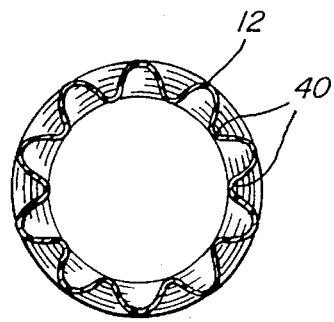
Figure 6:
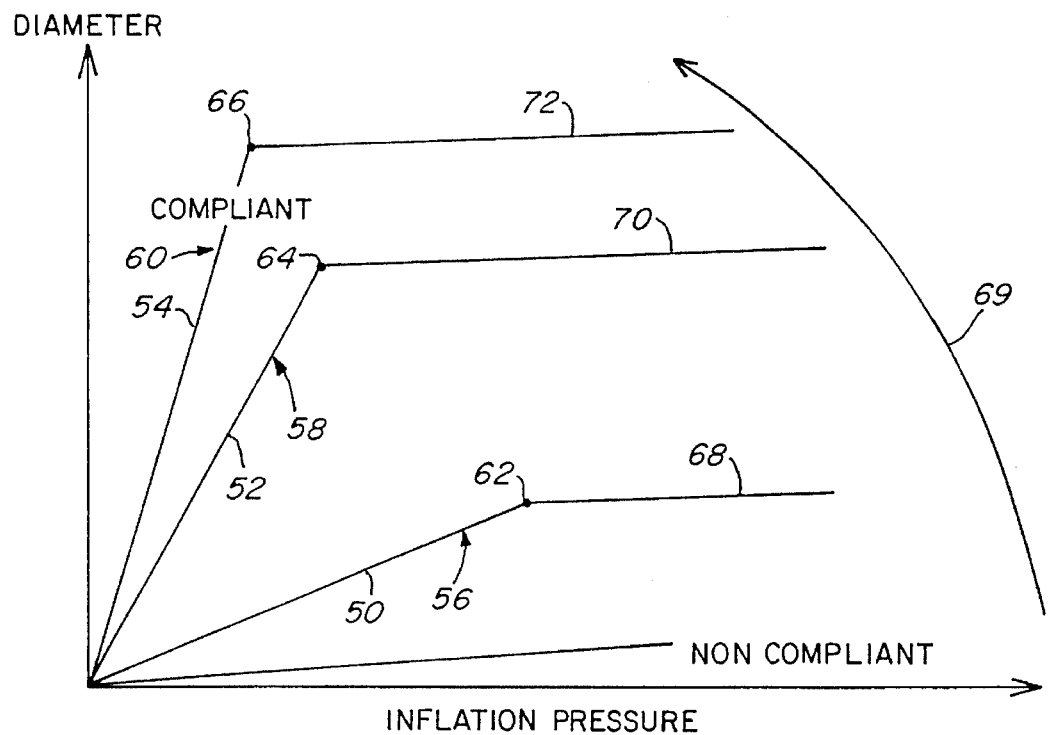
Figure 6A:
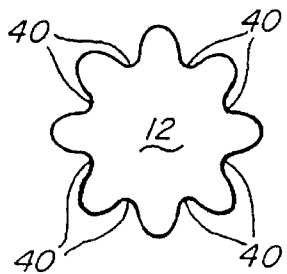
Figure 6B:
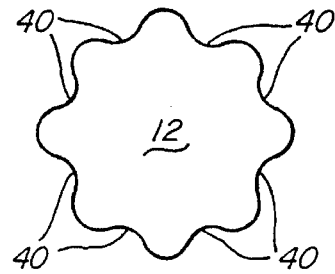
Figure 6C:
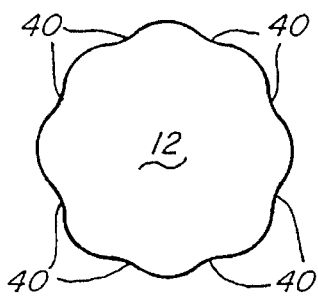
Figure 6D:
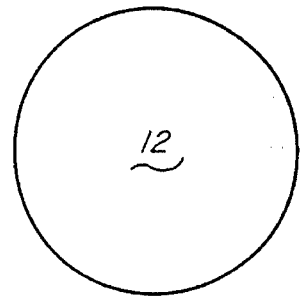
Figure 7A:
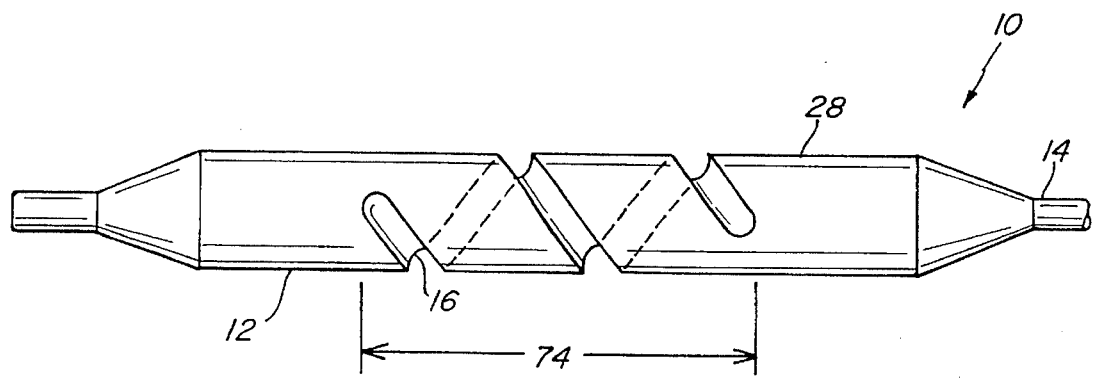
Figure 7B:
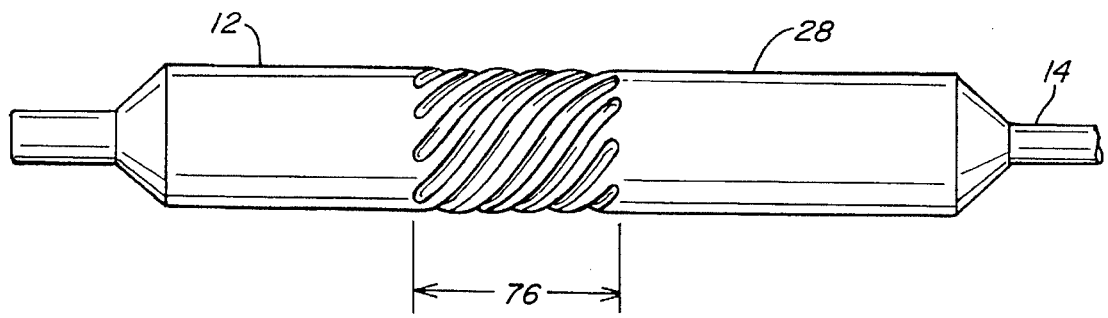

FIG. 1 illustrates a dilatation balloon of the present invention incorporating a single helical groove;

FIG. 2 illustrates the dilatation balloon of FIG. 1 in place in a curved blood vessel showing how the dilatation balloon conforms to the shape of the blood vessel;

FIG. 3 illustrates a dilatation catheter of the present invention having multiple helical grooves extending parallel to each other;

FIG. 4 illustrates a dilatation balloon of the present invention incorporating criss-crossed helical grooves extending in opposite directions;

FIGS. 5A and 5B illustrate a dilatation balloon of the present invention having a high degree of diametrical compliance;

FIG. 6 is a graph illustrating the relationship between pitch, width and depth of the helical groove, the number of helical grooves, and the degree of diametrical compliance imparted to the dilatation balloon;

FIGS. 6A, 6B, 6C, 6D illustrate, in cross-section, the manner in which helical grooves provide diametrical compliance; and FIG. 7A and 7B illustrate dilatation balloons similar to FIGS. 1 and 5 except that the helical groove extends over only a portion of the dilating surface of the dilatation balloon.

DETAILED DESCRIPTION

FIG. 1 illustrates a dilatation catheter 10 including a dilatation balloon 12 mounted on the distal end of a catheter shaft 14. A helical groove 16 extends the length of the balloon, preferably from a cone 18 to a cone 20. The groove 16 may extend into the cones 18 and 20. The helical groove 16 reduces the diameter of the dilatation balloon 12 in the grooved area and interrupts the diameter of a dilating surface 28 along the length of the balloon 12. The helical groove 16 is defined by a pitch, a width and a depth. The pitch refers to the longitudinal spacing 22 of the coils of the helical groove 16 in the dilating surface 28 of the dilatation balloon 12. The width refers to the distance 24 that the groove 16 interrupts the dilating surface 28. The depth 26 refers to how deeply the groove extends below the dilating surface 28 of the balloon 12. The helical groove 16 acts as a hinge, allowing the balloon 12 to bend and flex at any point along the length of the balloon regardless of inflation pressure. When dilating a lesion, the dilatation balloon 12 tends to conform to the natural curves of the blood vessel.

FIG. 2 illustrates the dilatation balloon 12 of FIG. 1 in place in a curved blood vessel 32. The catheter has been advanced to a point where the balloon 12 has crossed a stenosis or lesion 30. As illustrated in FIG. 2, the dilatation balloon 12 conforms to the shape of the blood vessel 32. As dilatation balloon 12 expands, the blood vessel 32 is also dilated with minimal straightening of the blood vessel due to the flexibility imparted by the helical groove 16.

FIG. 3 illustrates multiple helical grooves in dilatation balloon 12. In FIG. 3, two grooves, 16, 16A are illustrated. The grooves extend generally parallel to each other in the same direction longitudinally in the dilating surface 28 of the balloon 12. Where the helical grooves are spaced closer together along the longitudinal direction of the catheter as in regions 34, the dilatation balloon 12 is more flexible than in the regions 36 where the grooves are spaced further apart.

FIG. 4 illustrates a dilatation balloon 12 having multiple helical grooves wherein the multiple helical grooves 16, 16B extend generally opposite to one another in a criss-crossed fashion. The criss-crossed grooves help to reduce twisting of the dilatation balloon during inflation or deflation.

The helical groove not only allows the balloon to bend and flex at any region of the balloon, but also permits blood to perfuse downstream of the balloon during dilatation. Thus, the dilatation time during an angioplasty procedure can be increased because blood flow is maintained during dilatation. When used as a perfusion catheter, the helical groove should extend into each end portion cone 18, 20 to allow blood to perfuse through groove 16 past dilatation balloon 12. To increase the balloon's perfusion capability, the depth, width, and number of grooves may be increased.

The present invention also overcomes the very significant problem of "winging" that occurs with most conventional dilatation balloons. "Winging" refers to the formation of undesirable flat folds (wings), which extend outward from the rest of the catheter.

The helical groove permits the dilatation balloon 12 to deflate without winging. During deflation, the helical groove resists the tendency of the balloon to flatten and instead the balloon folds down tightly along the catheter body, resulting in a lower deflated profile. This allows the dilatation balloon 12 to be placed or pass through a stenosis that may prevent passage of a conventional balloon. The tendency to reduce winging is characteristic of all embodiments of the invention.

In another aspect of the invention, the helical groove may be used to impart diametrical compliance to the dilatation balloon 12. As illustrated in FIGS. 5A, 5B, by forming a number of small grooves 40 that wind tightly around the dilating surface of the balloon, the balloon can be made to be diametrically compliant wherein the inflated diameter of the dilatation balloon is a linear function of the inflation pressure. This aspect of the present invention is particularly advantageous when the dilatation balloon is constructed from a material such as polyethylene terephthalate (PET) or various nylons. PET is widely used as a material for dilatation catheter balloons because, depending upon the particular balloon mold used, there is a predetermined maximum diameter that the inflated balloon will attain. Further increases in the inflation pressure of the inflation fluid will not produce an increase in dilatation balloon diameter. However, PET is relatively non-compliant and a PET balloon does not exhibit diametrical compliance (that is, the maximum diameter of the dilatation balloon does not change significantly with changes in inflation pressure). In addition, the inflated diameter is not a linear function of inflation pressure. However, with the addition of one or more helical grooves in accordance with the present invention, a PET dilatation balloon becomes a "limited compliance balloon," meaning that it has diametrical compliance until a predetermined maximum diameter is reached and further increases in inflation pressure do not increase the inflated balloon diameter. The concept of controlled compliance will be better understood with reference to FIG. 6.

In other embodiments, a number of small grooves disposed in a criss-crossed manner such as illustrated in FIG. 4 or in a parallel manner such as illustrated in FIG. 3 may be used to impart diametrical compliance or to construct a limited compliance balloon.

As illustrated in FIG. 6, when helical grooves such as illustrated in FIG. 5 are incorporated into a dilatation balloon constructed of substantially non-compliant material, such as PET, the balloon exhibits diametrical compliance up until a predetermined limiting or maximum diameter is reached.

Inflation pressures above the level at which the limiting diameter is reached will not cause an increase in the diameter of the dilatation balloon. The dilatation balloon of the present invention has a linear diametrical compliance as illustrated by portions 50, 52, and 54 of respective curves 56, 58, and 60. Above a predetermined maximum diameter (points 62, 64, 66, respectively), increases in inflation pressure do not increase balloon diameter as illustrated by portions 68, 70, and 72 of curves 56, 58, and 60 respectively. As shown in FIG. 6, at arrow 69 increasing the pitch or depth of the helical groove or the number of helical grooves increases the diametrical compliance of the dilatation balloon, and vice versa. In addition, decreasing the width of the helical groove increases the diametrical compliance and vice versa. Thus, any degree of diametrical compliance and any limiting diameter within the working range of the balloon material may be obtained by choosing the proper combination of pitch, depth, width of the groove and the number of grooves in the surface of the dilatation balloon.

FIGS. 6A–6B illustrate how the helical grooves in the dilatation balloon 12 provide limited or controlled diametrical compliance. FIG. 6A illustrates, in cross-section, the dilatation balloon having a number of helical grooves 40 in the dilating surface 28. In FIG. 6A, the dilatation balloon 12 is in an uninflated or low pressure state. As inflation pressure is increased, the helical grooves 40 begin to gradually disappear as illustrated in FIGS. 6B and 6C. In FIG. 6D, dilatation balloon 12 is fully inflated and further increases in inflation pressure do not increase the diameter of the dilatation balloon. FIGS. 6A–6C represent diametrical compliance along the portions 50, 52, and 54 of curves 56, 58, and 60, respectively. FIG. 6D represents the diameter of the dilatation balloon at points 62, 64, or 66 of curves 56, 58, and 60, respectively. Beyond these points, as illustrated in FIG. 6, an increase in inflation pressure does not substantially increase the diameter of the dilatation balloon.

The addition of one or more helical grooves in accordance with the present invention makes the non-compliant PET or nylon balloon material perform like a compliant material, but with an upper limit on its size. This offers the clinical advantage of adjustable diameter without the risk of oversizing or rupturing at high pressures.

Use of a helical groove in a non-compliant material has been described, but the invention is not so limited. A helical groove could also be used to further control diametrical compliance in a dilatation balloon constructed of compliant material. In this case, the helical groove provides another dimension of control and the resulting diametrical compliance is a function of both the chosen material and the groove design.

As illustrated in FIGS. 7A and 7B, the helical groove may be provided in only a portion of the dilating surface of the dilatation balloon. As illustrated in FIG. 7A, helical groove 16 extends only over portion 74 of the dilatation balloon 12. This single, relatively large helical groove allows the dilatation balloon 12 to conform to the shape of a circuitous blood vessel only in region 74.

In FIG. 7B, a number of small, relatively low pitch helical grooves are formed in the dilating surface 28 of the dilatation balloon 12 only in region 76. Consequently, region 76 will provide a limited compliance type region whereas the remainder of the dilatation balloon 12 will provide essentially no diametrical compliance.

Dilatation balloons may be provided with helical grooves in multiple portions of the balloon longitudinally separated from one another to create zones of conformance/compliance. By varying the pitch, depth, and width of each helical groove as well as the number of helical grooves in zones 74, 76, a dilatation balloon can be constructed having zones that provide a combination of conformance and compliance depending upon overall catheter performance desired.

The present invention can be made using conventional blow molding techniques such as described in U.S. Pat. No. 4,490,421, which is incorporated herein by reference. According to one aspect of the present invention, dilatation balloons can be constructed to readily conform to curved blood vessels and perfuse blood past the dilatation balloon during dilation. For example, to create a perfusion balloon a single helical groove at a 45° pitch angle may be used in a balloon having a maximum diameter of 3 mm. The groove may be one millimeter deep, have a radius of 0.5 mm at the bottom and provide a 60° included angle from the bottom of the groove to the dilation surface. According to another aspect of the present invention, a degree of diametrical compliance can be provided in a dilatation balloon constructed of a non-compliant material to provide a limited compliance dilatation balloon. A compliant balloon may be provided in a dilatation balloon having a maximum diameter of 3 mm by providing a number of helical grooves each having a 45° pitch angle. Each of the helical grooves is longitudinally separated from one another by approximately 0.005 inches. The grooves may be 0.005 inches wide by 0.005 inches deep. These grooves give the balloon a corrugated look. The grooves may be run in the opposite direction as well in a criss-crossed type fashion. According to another aspect of the present invention, these two features can be combined by choosing the pitch, width, and depth of the helical groove as well as the number of helical grooves to provide a dilatation balloon that has a combination of conformance capability and diametrical compliance with an upper limit to the balloon diameter.

One particular advantage of the present invention, in one embodiment, is that it provides approximately 80% of the dilatation surface of a conventional straight dilatation balloon. By contrast, prior art conforming type balloons such as those shown in U.S. Pat. No. 4,983,167 use discrete balloons spaced longitudinally adjacent on the catheter shaft or a single balloon having regions of restricted diameter alternating with regions capable of producing radial dilating forces. These types of balloons provide only approximately 30% of the dilating surface of a conventional straight dilatation balloon. The relatively low and non-continuous dilating surface of prior art balloons may not produce a smooth luminal surface when dilating a lesion or stenosis in a bend in the blood vessel. By contrast, the present invention, with its much higher total dilating surface tends to produce smoother and more uniform dilation of the blood vessel lumen.

We have found that a helical groove in the dilatation surface of the dilatation balloon is the best way of achieving all of the advantages of the present invention. A helical groove provides uniform "hoop stress" around the perimeter of the fully inflated dilatation balloon. Hoop stress refers to the tangentially directed force created by the pressure and directed by the helical groove that maintains the circular cross-section of the balloon during inflation. The hoop stress controls the diameter of the dilatation balloon so that inflation pressure inside the balloon results in a uniform balloon diameter over the dilatation surface for any given inflation pressure.

The invention thus provides perfusion of blood past the dilatation balloon and avoidance of straightening of the blood vessel when the dilatation balloon is inflated. In addition, the present invention allows diametrical compliance to be controlled and designed into the dilatation balloon. Another advantage is that the use of one or more helical grooves allows the dilatation balloon to be deflated without winging.

It should be understood that the foregoing description of the invention is intended merely to be illustrative thereof and that other embodiments, modifications and equivalents may be apparent to those skilled in the art without departing from its spirit.

Having thus described the invention what we desire to claim and secure by letters patent is:

1. A method of dilating a blood vessel with a dilatation catheter comprising the steps of:

positioning in the blood vessel a dilatation catheter having a limited compliance dilatation balloon dimensioned to dilate the lumen of the blood vessel when inflated, the balloon having a dilating surface and including at least one helical groove disposed in at least a portion of the dilating surface, the portion of the balloon that defines the groove being constructed to deflect and cause the groove to diminish in depth with increased inflation pressure to enable the effective dilating diameter of the balloon to increase within a limited range of diameters; and inflating the limited compliance dilatation balloon to dilate the blood vessel.

2. The method of claim 1 further comprising a step of varying the diameter of the limited compliance dilatation balloon by varying the pressure of an inflation fluid in the dilatation balloon.

3. The method of claim 2, wherein the diameter of the limited compliance dilatation balloon varies as a linear function of the pressure until a predetermined maximum diameter is reached.

4. The method of claim 3 wherein the limited compliance dilatation balloon is constructed of a substantially non-compliant material.

5. The method of claim 4, wherein the material is polyethylene terephthalate.

6. The method of claim 1 wherein the blood vessel is curved and wherein the limited compliance dilatation balloon, when inflated, conforms to the curvature of the blood vessel and dilates the blood vessel without straightening the blood vessel.

7. The method of claim 3, further comprising the step of providing perfusion of blood through the helical groove during dilation of the blood vessel.

8. A dilatation catheter comprising:

a catheter shaft having a distal end;

a limited compliance dilatation balloon mounted on the distal end of the catheter shaft, the balloon being dimensioned to dilate a lumen of a blood vessel when inflated;

the balloon having a dilating surface and including at least one helical groove disposed in at least a portion of the dilating surface of the balloon wherein the at least one helical groove includes at least one of a pitch, width and depth selected to facilitate deflection and reduction in the depth of the groove with increased inflation pressure to enable the diameter of the balloon to increase, thereby to control the effective dilating diameter of the balloon.

9. The dilatation catheter of claim 8 wherein the at least one helical groove is disposed in at least one selected portion of the dilating surface of the balloon to provide a zone of diametrical compliance only in the selected portion.

10. The dilatation catheter of claim 9 wherein the at least one helical groove is disposed in each of a plurality of selected portions of the dilating surface of the balloon to provide a plurality of zones of diametrical compliance.

11. The dilatation catheter of claim 8, wherein at diameters less than a predetermined maximum diameter of the limited compliance dilatation balloon, the diameter of the limited compliance dilatation balloon is a linear function of inflation pressure.

12. The dilatation catheter of claim 11 wherein the pitch and depth of the at least one helical groove are such that increasing at least one of them increases the diametrical compliance of the balloon and wherein decreasing at least one of them decreases the diametrical compliance of the limited compliance dilatation balloon.

13. The dilatation catheter of claim 12 wherein the pitch and depth of the at least one helical groove are such that decreasing its width increases the diametrical compliance of the balloon and wherein increasing its width decreases the diametrical compliance of the balloon.

14. The dilatation catheter of claim 13, wherein the at least one helical groove includes multiple helical grooves.

15. The dilatation catheter of claim 14 wherein the helical grooves are constructed such that increasing their number increases the diametrical compliance of the balloon and decreasing their number decreases the diametrical compliance of the balloon.

16. The dilatation catheter of claim 13, wherein the multiple helical grooves extend parallel to each other in the dilating surface.

17. The dilatation catheter of claim 13, wherein the multiple helical grooves are not parallel to each other in the dilating surface.

18. The dilatation catheter of any one of claims 8–17 wherein the balloon is constructed of a substantially non-compliant material.

19. The dilatation catheter of claim 18, wherein the material is polyethylene terephthalate.

20. The dilatation catheter of either one of claims 8 or 5 wherein at least one of the pitch, width and depth of the at least one helical groove varies over the dilating surface of the limited compliance dilatation balloon.

21. A limited compliance dilatation catheter balloon having a dilating surface, comprising:

at least one helical groove disposed in at least a portion of the dilating surface of the balloon wherein the pitch, width and depth of the at least one helical groove is selected to facilitate deflection and reduction in the depth of the groove with increased inflation pressure to enable the diameter to increase thereby to compliantly control the effective dilating diameter of the balloon.

22. The limited compliance dilatation catheter balloon of claim 21, wherein the at least one helical groove is disposed in at least one selected portion of the dilating surface of the balloon to provide a zone of diametrical compliance only in the selected portion.

23. The limited compliance dilatation catheter balloon of claim 22 wherein the at least one helical groove is disposed in each of a plurality of selected portions of the dilating surface of the balloon to provide a plurality of zones of diametrical compliance.

24. The limited compliance dilatation catheter balloon of claim 21, wherein at diameters less than a predetermined maximum diameter of the limited compliance dilatation catheter balloon, the diameter of the limited compliance dilatation catheter balloon is a linear function of inflation pressure.

25. The limited compliance dilatation catheter balloon of claim 24 wherein the pitch and depth of the at least one helical groove are such that increasing at least one of them increases the diametrical compliance of the balloon and wherein decreasing at least one of them decreases the diametrical compliance of the balloon.

26. The limited compliance dilatation catheter balloon of claim 25 wherein the pitch and depth of the at least one helical groove are such that decreasing its width increases the diametrical compliance of the balloon and wherein increasing its width decreases the diametrical compliance of the balloon.

27. The limited compliance dilatation catheter balloon of claim 26 wherein the balloon includes multiple helical grooves.

28. The limited compliance dilatation catheter balloon of claim 27 wherein the helical grooves are constructed such that increasing their number increases the diametrical compliance of the balloon and decreasing their number decreases the diametrical compliance of the balloon.

29. The limited compliance dilatation catheter balloon of claim 27, wherein the multiple helical grooves extend parallel to each other in the dilating surface.

30. The limited compliance dilatation catheter balloon of claim 27, wherein the multiple helical grooves are not parallel to each other in the dilating surface.

31. The dilatation catheter balloon of any one of claims 21–30 wherein the balloon is constructed of a substantially non-compliant material.

32. The limited compliance dilatation catheter balloon of claim 31 wherein the material comprises polyethylene terephthalate.

33. A method of dilating a blood vessel with a dilatation catheter comprising the steps of:

positioning a dilatation catheter having a deflated limited compliance dilatation balloon adapted to dilate a lumen of a blood vessel when inflated, the balloon including at least one helical groove disposed in at least a portion of a dilating surface of the balloon, the groove being constructed to deflect and diminish in depth with increased inflation pressure to enable the diameter of the balloon to increase and enable the balloon to be substantially free of flat folds when deflated; and inflating the limited compliance dilatation balloon to dilate the blood vessel.

34. The method of claim 33 further comprising a step of varying a diameter of the balloon by varying the pressure of an inflation fluid in the dilatation balloon.

35. The method of claim 34, wherein the diameter of the limited compliance dilatation balloon varies as a linear function of the pressure until a predetermined maximum diameter is reached.

36. The method of claim 35 wherein the balloon is constructed of a substantially non-compliant material.

37. The method of claim 33 wherein the blood vessel is curved and wherein the balloon, when inflated, conforms to the curvature of blood vessel and dilates the blood vessel without straightening the blood vessel.

38. A dilatation catheter comprising:

a catheter shaft having a distal end;

a limited compliance dilatation balloon mounted on the distal end of the catheter shaft, the balloon having a dilating surface and being adapted to dilate the lumen of a blood vessel when inflated;

the dilating surface of the balloon including at least one helical groove disposed in at least a portion of the dilating surface wherein the pitch and depth of the helical groove is selected to facilitate deflection and reduction in the depth of the groove with increased inflation pressure to enable the diameter to increase thereby to control the effective dilating diameter of the balloon the balloon, when deflated, being substantially free of flat folds.

39. The dilatation catheter of claim 38 wherein the at least one helical groove is disposed in at least one selected portion of the dilating surface of the balloon to provide a zone of diametrical compliance only in the selected portion.

40. The dilatation catheter of claim 39 wherein the at least one helical groove is disposed in multiple selected separate portions of the dilating surface of the balloon to provide a respective zone of diametrical compliance in each of the selected separate portions.

41. The dilatation catheter of claim 38 wherein at diameters less than a predetermined maximum diameter of the balloon, the diameter of the balloon is a linear function of inflation pressure.

42. The dilatation catheter of claim 41 wherein the pitch and depth of the at least one helical groove are such that increasing at least one of them increases the diametrical compliance of the balloon and wherein decreasing at least one of them decreases the diametrical compliance of the balloon.

43. The dilatation catheter of claim 42 wherein the pitch and depth of the at least one helical groove are such that decreasing its width increases the diametrical compliance of the balloon and wherein increasing its width decreases the diametrical compliance of the balloon.

44. The dilatation catheter of claim 43 wherein there are multiple helical grooves.

45. The dilatation catheter of claim 43 wherein increasing the number of helical grooves increases the diametrical compliance of the balloon and decreasing the number of helical grooves decreases the diametrical compliance of the balloon.

46. The dilatation catheter of claim 44 wherein the multiple helical grooves extend parallel to each other in the dilating surface.

47. The dilatation catheter of claim 44 wherein the multiple helical grooves are not parallel to each other in the dilating surface.

48. The dilatation catheter of any one of claims 38–47 wherein the limited compliance dilatation balloon is constructed of a material that is substantially non-compliant.

49. The dilatation catheter of claim 48 wherein the material is polyethylene terephthalate.

50. A limited compliance dilatation catheter balloon adapted to dilate a blood vessel lumen when inflated and having a dilating surface, comprising:

at least one helical groove disposed in at least a portion of the dilating surface of the balloon, the at least one helical groove having at least one of a pitch, width and depth selected to control the diametrical compliance of the balloon;

the at least one groove enabling the balloon to be substantially free of flat folds when the balloon is deflated.

51. The dilatation catheter of either one of claims 38 or 50 wherein at least one of the pitch, width and depth of the at least one helical groove varies over the dilating surface of the balloon.

52. The limited compliance dilatation catheter balloon of claim 50 wherein the at least one helical groove is disposed in at least one selected portion of the dilating surface of the balloon to provide a zone of diametrical compliance only in the selected portion.

53. The limited compliance dilatation catheter balloon of claim 51 wherein the at least one helical groove is disposed in multiple selected separate portions of the dilating surface of the balloon to provide a respective zone of diametrical compliance in each of the selected separate portions.

54. The limited compliance dilatation catheter balloon of claim 50 wherein at diameters less than a predetermined maximum diameter of the balloon, the diameter of the balloon is a linear function of inflation pressure.

55. The limited compliance dilatation catheter balloon of claim 55 wherein the pitch and depth of the at least one helical groove are such that increasing at least one of them increases the diametrical compliance of the balloon and wherein decreasing at least one of them decreases the diametrical compliance of the balloon.

56. The limited compliance dilatation catheter balloon of claim 55 wherein the pitch and depth of the at least one helical groove are such that decreasing its width increases the diametrical compliance of the balloon and wherein increasing its width decreases the diametrical compliance of the balloon.

57. The limited compliance dilatation catheter balloon of claim 56, wherein the at least one helical groove includes multiple helical grooves.

58. The limited compliance dilatation catheter balloon of claim 57 wherein increasing the number of helical grooves increases the diametrical compliance of the balloon and decreasing the number of the helical grooves decreases the diametrical compliance of the balloon.

59. The limited compliance dilatation catheter balloon of claim 57, wherein the multiple helical grooves extend parallel to each other in the dilating surface.

60. The limited compliance dilatation catheter balloon of claim 57, wherein the multiple helical grooves are not parallel to each other in the dilating surface.

61. The dilatation catheter balloon of any one of claims 50–60 wherein the balloon is constructed of a substantially non-compliant material.

62. The limited compliance dilatation catheter balloon of claim 61, wherein the material in polyethylene terephthalate.

63. A method of dilating a blood vessel as defined in claim 1 wherein the balloon includes only a single helical groove.

64. A dilatation catheter as defined in claim 8 wherein the balloon includes only a single helical groove.

65. A limited compliance dilatation catheter balloon as defined in claim 21 wherein the balloon includes only a single helical groove.

66. A method of dilating a blood vessel with a dilatation catheter as defined in claim 33 wherein the balloon has only a single helical groove.

67. A dilatation catheter as defined in claim 38 wherein the balloon has only a single helical groove.

68. A limited compliance dilatation catheter balloon as defined in claim 50 wherein the balloon includes only a single helical groove.

69. A method dilating blood vessel with the dilatation catheter is defined in claim 1 wherein at least one of the pitch, width and depth of the least one helical groove varies over the dilating surface of the limited compliance dilatation balloon.

70. A method of dilating a blood vessel with dilatation catheter is defined in claim 33 wherein at least one of the pitch, width and depth of the at least one helical groove varies over the dilating service of the balloon.

* * * * *